United States Patent [19]
Huh et al.

[11] Patent Number: 5,750,359
[45] Date of Patent: May 12, 1998

[54] COMPOSITION FOR DETECTING LEUCOCYTE AND PROTEINASE IN URINE AND ITS MEASURING DEVICE

[75] Inventors: Nam Won Huh; Yong Ae Park; Yong Ho Kim, all of Pusan, Rep. of Korea

[73] Assignee: Chung-Do Pharmaceutical Co., Ltd., Kyungsangnam-do, Rep. of Korea

[21] Appl. No.: 756,370

[22] Filed: Oct. 25, 1996

[30] Foreign Application Priority Data

Jul. 30, 1996 [KR] Rep. of Korea .................. 96-31386

[51] Int. Cl.$^6$ .................. C12Q 1/44; C12Q 1/37
[52] U.S. Cl. .................. 435/19; 435/23
[58] Field of Search .................. 435/4, 19, 23, 435/805, 29

[56] References Cited

U.S. PATENT DOCUMENTS 4,657,855  4/1987  Corey et al. .
5,464,739  11/1995  Johnson et al. .................. 435/4

FOREIGN PATENT DOCUMENTS 7242639  9/1995  Japan .
812961   6/1981  South Africa .

Primary Examiner—Ralph Gitomer
Attorney, Agent, or Firm—Gary M. Nath; Nath & Associates; Suet M. Chong

[57] ABSTRACT

With the recognition that like esterase, the thiazole derivatives show a strong nucleophilicity owing to sufficient electronic density in heterocycle, when its ester is degraded by some enzymes. The composition for detecting leucocyte and proteinase in urine has been developed, which contains a thiazole derivative. According to this invention, the thiazole derivative may be synthesized as an ester form by combining both the well-known thiazolone derivative and amino acid derivatives as starting materials. Now that the method for manufacturing the thiazole derivative is simple and general, the mass-scale production may be available within a short period of time. Further, in case of the measuring device produced according to this invention, the application method is simple and diagnostic performance is superior.

7 Claims, No Drawings

COMPOSITION FOR DETECTING LEUCOCYTE AND PROTEINASE IN URINE AND ITS MEASURING DEVICE

FIELD OF THE INVENTION

This invention relates to a novel composition and its measuring device, designed for detecting the presence of leucocyte generated by the inflammation in urinary organs as well as leucocyte esterase and some other proteinase in tile ml 1k associated with bovine breast inflammation in a prompt and sensitive manner.

DESCRIPTION OF THE RELATED ART

In general, since the presence of leucocyte in urine of patients is associated with infection or malfunction in the kidney or urinary tract, its accurate detection has a significant meaning for the physiological treatment or diagnosis on the part of doctors.

To this end, a basic method to measure the number of leucocyte in precipitation or centrifuged compound of urine by microscope has been widely available hitherto. In spite of the fact that said method has a reliance in the accuracy of diagnosis, however, the following disadvantages cannot be neglected:

a) To install the proper devices for measurement, enormous expenditures should be invested together with a lengthy time, and b) Since leucocyte has 60 minutes in its half life, misdiagnosis as negative may occur in patients urine with a lapse of a certain time or lower calculation than actual figure.

In view of these situations, various methods have been suggested in an attempt to diagnose leucocyte easily, conveniently and with relatively high accuracy. The fundamental research is chiefly oriented in the following method, i.e., when a specific chemical substance, a substrate, is degraded by various enzymes present in the leucocyte, an indicator is used to cause the color change; or when degraded compounds undergo the second reaction, the presence of leucocyte and its amount may be detected by the color development. Such method is disclosed in the U.K. Patent (No. 1, 128, 371), U.S. Pat. (No. 3,087,794; U.S. Pat. No. 4,278, 763; U.S. Pat. No. 4,704,460) and various publications (F. Schmalzl, H. Braunsteiner, Klin. Wscher., 46, 642 (1968).; Janoff et. al. Proc. soc. Exper. Bio. Med., 136, 1045–1049 (1971).

First, the U.S. Pat. No. 3,87,794 discloses that the presence of leucocyte may be diagnosed by peroxidase contained in a granular leucocyte, through the manifestation of colored oxidative product in a filter paper stained with hydrogen peroxide and o-tolidin. However, its actual application may not be available due to reductive materials in urine and safety problems involved with peroxidase itself.

Thereafter, the methods designed to confirm the presence of esterase in leucocyte have been attempted for the past several years. According to such methods, ester compound showing colorless or pale color is allowed to be degraded into colorless acid moiety and alcoholic moiety by esterase. Then, under diazonium or oxidative reaction, the alcoholic moiety is converted to the 2nd thick colored product so as to ascertain the presence of leucocyte and its amount by the naked eye.

The initiation of this method was derived from the introduction of a method in which naphtol-AS-D chloroacetate was used as a substrate and when chloroacetate was isolated by some enzymes, colored azo compound was formed by diazonium salt (F. Schmalzl, H. Braunsteiner, Klin. Wscher., 46, 642 (1968). However, this method has also recognized some disadvantages in the clinical application, since there is a possibility that diazonium salt may be reacted with urobilinogen or bilirubin contained in urine and to confirm the leucocyte by naked eye, more than 5000 cells/µl should be necessary.

Similarly, the U.K. No. 1,128,371 discloses that colorless indoxyl or thioindoxylester is allowed to be degraded into indoxyl or thioindoxyl by esterase. Then, thick colored indigo or thioindigo may he produced by oxygen in the air or oxidizer. However, this method also fails to detect the number of leucocyte containing less than 10,000 cells/µl within two minutes. Nonetheless, it has been suggested through this patent that if a variety of acid moeities from ester compound used as a substrate may be selected, more effective enzymatic activity proves to be induced. The acid moiety profiles were ascertained by the intensive study of Jacoff et. al and as a result, alanine derivatives proved to be most effective acid moiety degraded by esterase.

With these theories in combination, the U.S. Pat. No. 4,278,763 suggests a method of using indoxyl or thioindoxylamino acid ester as a substrate. Further, the U.S. Pat. No. 4,704,460 discloses that amino acid ester of pyrrole derivatives is employed as a substrate and if diazonium salt is added to pyrrole derivatives degraded by enzyme, its color may be changed to thick violet. With tile addition of nucleophilic alcohols such as decanol, greatly facilitated reaction speed may lead to detecting the number of leucocyte by 10 cells/µl within 90 seconds. Currently, each preparation using said two patent processes has predominated the leucocyte based diagnostic reagents market in the world. However, the synthesis of two substrates available in the above two patent processes is very difficult with the following demerits:

Indoxyl ester: Since the reactivity of 3-hydroxyindole, intermediate in synthesis, is very great, indigo in thick blue color or macromolecules may be produced due to sensitive oxidative reaction by oxygen in the solvent or the air, the final yield is very low, even though the reaction is conducted under inert gas after the deoxydation of all solvents.

Pyrrole: Since this substance undergo a similar side-reaction as above, a trace amount of final product may be obtained, even though a lengthy period of time is required in the synthesis. The whole process is very complicated, while requiring the highly sophisticated synthesis technology. Further, in case that the number of leucocyte is in the level of 10 cells/µl in urine, the discolored scope is quite minute and urine color itself may lead to confusion.

SUMMARY OF THE INVENTION

With the recognition that like esterase, the thiazole derivatives show a strong nucleophilicity owing to sufficient electronic density in heterocycle, when its ester is degraded by some enzymes. The inventor et al. has succeeded in developing the composition for detecting leucocyte and proteinase in urine, which contains a thiazole derivative. According to this invention, the thiazole derivative may be synthesized as an ester form by combining both the well-known thiazolone derivative and amino acid derivatives as starting materials. Now that the method for manufacturing the thiazole derivative is simple and general, the mass-scale production may be available within a short period of time. Further, in case of the measuring device produced according to this invention, the application method is simple and diagnostic performance is superior.

This invention is described in more detail as set forth hereunder.

According to this invention, said composition contains a thiazole derivative expressed by the following formula.

$$\underset{R_1}{\overset{N}{\bigwedge}}\overset{O-A}{\underset{S}{\diagup}} \quad (1)$$

Wherein,

A is a N-blocked-amino acid residue, $R_1$ is substituted or non-substituted benzene ring.

In an effort to prepare said compound, thiazole derivatives may be employed as an starting material. The method for manufacturing thiazolone has been already known by Jansen et al. and its obtainment may be available by reacting both carboxymethyl thiobenzimidate hydrobromide and pyridine.

As illustrated in the following scheme (1), reaction may be initiated by the use of starting materials, well known compounds, such as the thiazolone derivative of the general formula (2), so formed as above, and chloride of amino acid derivative of the general formula (3). Each substance dissolved in solvents is cooled and mixed slowly. This reaction mixture is allowed to be stirred, followed by several hours' standing at room temperature. The solution is washed, dried and filtered for concentration under reduced pressure. The solid, so formed, is dissolved in acetone and with the addition of hexane, the reaction mixture is allowed to stand at low temperature for about 1 hour, in order to remove the hemisolid impurity, so formed. Another hexane is added to the residue, followed by 10 hours' standing in the refrigerator. The filtration of needle crystals, so formed, gives a desired compound.

Meantime, the large reactivity of thiazolone derivatives may lead to a poor yield due to the occurrence of dimerization or multimerization even in $$\underset{R^1}{\overset{N}{\bigwedge}}\overset{O}{\underset{S}{\diagup}} + A-Cl \longrightarrow \underset{R^1}{\overset{N}{\bigwedge}}\overset{O-A}{\underset{S}{\diagup}}$$

(2)      (3)           (1)

the process of their recrystallization but to comply with this matter, the ester synthesis with the compound of general formula (3) is attempted so as to isolate pure substances from the final product without purifying thiazolone of general formula (2), so formed, thus further enhancing the yield. In contrast to this, the aforementioned indole or pyrrole derivatives have recognized some disadvantages in that under the circumstances where a lot of side reactions occur in the process of manufacturing their intermediates, the reaction mechanism is very complicated and their yield proves to be poor. However, in line with the synthesis of the thiazole derivative, a substrate of this invention, its whole process is very simple so that larger amounts of final product may be obtained by a general method within a short period of time. Also, since the presence of leucocyte may be clearly manifested by the development of color, this invention is quite effective for the diagnosis of leucocyte in small amount.

The thiazole derivative, so synthesized as aforementioned, has a reactivity very similar to the conventional indole or pyrrole derivatives and for a novel diagnosis method, a simple paper mixing with octanediol as accelerator and diazonium salt may be manufactured. According to this invention, further, diazonium salt may be used. Since the diazonium salt has been well known to produce azo dyes by combining with alcohol, it may be used for some color-developing technology using azo dyes which may be manufactured from the following process: thiazole ester of this invention is hydrolyzed by esterase, the formed thiazole is combined with diazonium salt to give the azo dyes. Said diazonium salt is characterized by the following properties:

The electrophilic character of diazonium salt employed in this invention is relatively weak;

Any interference with urobilinogen or bilirubin should not occur in a weak alkali solution;

After degradation of thiazole ester, diazo-coupling may occur by the effect of a strong nucleophilicity of thiazole so formed.

The diazonium salts, which may be used for this invention, are 1-diazo-8-naphtol-3,6-disulfonic acid, chloride, zinc chloride double salt and 6-diazo-1-naphtol-3-sulfonic acid, chloride double salt.

The composition of this invention may be generally used by its sedimentation into the measuring device. For the manufacture of said composition, a mixture of NaCl, boric acid and polyvinylpyrrolidone is deposited as the first solution and then, a dried filter paper is further deposited into previously prepared solution.

This invention is explained in more detail by the following examples, but the claims are not limited to these examples.

EXAMPLE

1) N-tosyl-L-alanine 100 g of p-toluene sulfonyl chloride in 200 ml of toluene was slowly added to 50 g (0.505 mole) of L-alanine dissolved in 1 l 1N-sodium hydroxide cooled to below 5° C. and stirred at room temperature for 24 hours. Then, the aquose layer was cooled to below 5° C. and with a slow addition of concentrated hydrochloric acid, pH was adjusted to 1.5. After standing in the refrigerator for 3 to 4 hours, the white solid, so formed, was filtered, washed with water sufficiently and dried.

Yield: 72%, mp=135° C. IR (cm−1) 1726, 1340, 1164, 1095 1H NMR (DMSO d6, ppm) 7.75 (d, 2H), 7.41 (d, 2H), 6.4 (d, 1H), 3.85 (m, 1H), 2.40 (s, 3H), 1.20 (d, 2H)

2) N-tosyl-L-alanyl chloride 10 g (42 mmol) of N-tosyl-L-alanine and 6 to 7 drops of DMF were dissolved in 100 ml of dichloromethane and 3 ml of oxalyl chloride was added by dropwise under $N_2$ gas. After 2 hrs, reaction mixture was evaporated. The solid residue, so formed, is dissolved in a small amount of chloroform, followed by the addition of purified hexane to obtain a white solid.

Yield: 94% mp=100° C. IR (cm$^{-1}$) 3360, 3260, 3025, 1775, 1605, 1350, 1170, 909 1H NMR (CDCl3, ppm) 7.76 (d, 2H), 7.31 (d, 2H), 5.93 (d, 1H), 4.33 (m, 1H), 2.43 (s, 3H), 1.48 (d, 3H)

3) 2-phenyl-4(5H)-thiazolone

Thiobenzamide (15 g) and bromoacetic acid (15 g) were synthesized with a method of Jensen, K. A., Crossland, 1., Acta Chem. Scand., 17, 144–162 (1963). Yield: 8.14 g (42%)

4) 2-phenyl-4(N-tosyl-L-alanyloxy)-thiazole 4.43 g (0.025 mole) of 2-phenyl-4(5H)-thiazolone was dissolved in a cosolvent of 150 ml of dichloromethane and 6 ml of pyridine and cooled to 5° C. The solution of N-tosyl-L-alanyl chloride (10 g) dissolved in dichloromethane cooled to below was added to the mixture. The reacting solution was stirred, followed by standing at room temperature for 3 hours. The solution was washed with 1N citric acid, water, 5% sodium bicarbonate and a saturated sodium chloride solution in that order, dried over magnesium sulfonate, filtered; and concentrated under reduced pressure. Yellowish solid residue, so formed, was dissolved in 50 ml of acetone, and 50 ml of hexane was added to the solution. After standing the solution at room temperature for 1 hour, the thick yellowish amorphous solid, so formed, was removed. 200 ml of another hexane was added to the filtrate, followed by 10 hours' standing in the refrigerator. Filtration gave pale yellowish needle crystals as a desired compound.

Yield: 4.78 g (42%) mp=110°~112° C. IR (cm$^{-1}$) 3290, 3120, 1760, 1500, 1340, 1188, 1160, 770 1H NMR (CDCl3, ppm) 7.89 (s, 2H), 7.80 (d, 2H), 7.46 (s, 3H), 7.27 (m, 2H), 6.92 (s, 1H), 5.41 (d, 1H), 4.31 (m, 1H), 2.37 (s, 3H), 1.59 (d, 3H).

5) 1-diazo-8-naphtol-3,6-disulfonic acid, chloride, zinc chloride double salt 25.5 g of 4-Amino-5-hydroxy-2,7-naphthalene disulfonic acid, disodium salt was suspended in 100 ml of 6N-hydrochloric acid, and the solution of sodium nitrite(6 g) dissolved in 12 ml of water was added to the mixture by dropwise for 0.5 hr. 21.4 g(62.5%) of yellowish crystals was produced by adding ZnCl$_2$ to diazonium salt solution, so formed. mp=107°~109° C.

6) 6-diazo-1-naphtol-3-sulfonic acid, chloride double salt

The starting material is 7-amino-4-hydroxy-2-naphthalenesulfonic acid and the same method of example 5 was used. Yield 63% mp=117°~119° C.

Preparation of testing paper

In order to detect the presence of leucocyte in urine, optional conditions were provided to prepare a polystyrene strip. A small type of testing paper in a regular square was attached to the end of its strip, and sedimented and dried by the following two mixing solutions successively. 1st solution (100 ml of aqueous solution) 3% (w/v) Sodium chloride 5% (w/v) Boric acid (pH 7.7) 2% (w/v) Polyvinyl pyrrolidone (K-10) The sedimented paper was dried by heating at 60° C. for 10 minutes. 2nd solution (100 ml of acetone) A 0.06% (w/v) 2-phenyl-4(N-tosyl-L-ananyloxy)-thiazole 0.05% (w/v) 2-methoxy-4-molpholinobenzene diazonium chloride zinc chloride disalts 1.0% (w/v) 1.8 octanediol The second-sedimented paper was dried by heating at 50° C. for 5 minutes.

When leucocyte-containing urines were stained to the testing filter paper, so manufactured as aforementioned, the violet color began to appear gradually in about 10 seconds and with the lapse of about 1 minute, the color degrees per stage were completely identified according to the amounts of leucocyte. The identification was available to 10 cells/hpf at the minimum and based upon the results that the reflection value in a spectroscope showed the distance of more than 30%, the scope of deviation may he significantly narrowed when the device was read. This clinical trials were not affected by various chemical substances contained in urine.

What is claimed is:

1. Composition for detecting leucocytes and proteinase in urine, which contains a compound having the following formula (1) or pharmaceutically acceptable salts and solvated salts

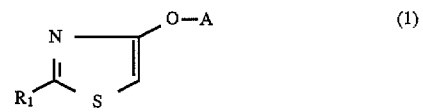

wherein;

A is a N-blocked-amino acid residue,

R1 is substituted or non-substituted benzene ring.

2. Composition for detecting leucocytes and proteinase in urine according to claim 1, wherein diazonium salt is employed as a color-developing agent.

3. Composition for detecting leucocytes and proteinase in urine according to claim 2, wherein said diazonium salt is 1-diazo-8-naphtol-3,6-disulfonic acid, chloride, zinc chloride double salt.

4. Composition for detecting leucocytes and proteinase in urine according to claim 2, wherein said diazonium salt is 6-diazo-1-naphtol-3-sulfonic acid, chloride double salt.

5. Composition for detecting leucocytes and proteinase in urine according to claim 1, wherein said diazonium salt is 1-diazo-8-naphtol-3,6-disulfonic acid, chloride, zinc chloride double salt.

6. Composition for detecting leucocytes and proteinase in urine according to claim 1, wherein said diazonium salt is 6-diazo-1-naphtol-3-sulfonic acid, chloride double salt.

7. The measuring device for detecting leucocytes and proteinase in urine, which attach a filter paper sedimented and dried by mixing solutions comprising the compound of following formula (1) or pharmaceutically acceptable salts and solvated salts

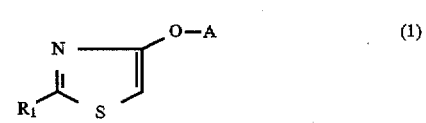

wherein;

A is a N-blocked-amino acid residue,

R$_1$ is substituted or non-substituted benzene ring.

* * * * *